US011676722B1

(12) United States Patent
Adib et al.

(10) Patent No.: US 11,676,722 B1
(45) Date of Patent: Jun. 13, 2023

(54) METHOD OF EARLY DETECTION, RISK STRATIFICATION, AND OUTCOMES PREDICTION OF A MEDICAL DISEASE OR CONDITION WITH MACHINE LEARNING AND ROUTINELY TAKEN PATIENT DATA

(71) Applicant: Biocogniv Inc., Burlington, VT (US)

(72) Inventors: Artur B. Adib, South Burlington, VT (US); Tanya S. Kanigan, Shelburne, VT (US); Robert A. Levine, Guilford, CT (US)

(73) Assignee: Biocogniv Inc., Burlington, VT (US)

(*) Notice: Subject to any disclaimer, the term of this patent is extended or adjusted under 35 U.S.C. 154(b) by 0 days.

(21) Appl. No.: 17/210,382

(22) Filed: Mar. 23, 2021

Related U.S. Application Data

(60) Provisional application No. 63/023,132, filed on May 11, 2020, provisional application No. 62/993,671, filed on Mar. 23, 2020.

(51) Int. Cl.
| | | |
|---|---|---|
| *G16H 50/20* | (2018.01) | |
| *G16H 10/60* | (2018.01) | |
| *G16H 10/40* | (2018.01) | |
| *G16H 50/30* | (2018.01) | |
| *A61B 5/15* | (2006.01) | |

(52) U.S. Cl.
CPC .............. *G16H 50/20* (2018.01); *A61B 5/15* (2013.01); *G16H 10/40* (2018.01); *G16H 10/60* (2018.01); *G16H 50/30* (2018.01)

(58) Field of Classification Search
CPC ........ G16H 50/20; G16H 10/40; G16H 10/60; G16H 50/30
See application file for complete search history.

(56) References Cited

U.S. PATENT DOCUMENTS

| | | | |
|---|---|---|---|
| 2005/0137481 A1* | 6/2005 | Sheard | G16H 40/67 600/508 |
| 2006/0025931 A1* | 2/2006 | Rosen | G16H 50/20 702/19 |
| 2006/0224532 A1* | 10/2006 | Duan | G06N 3/08 706/15 |
| 2006/0289342 A1* | 12/2006 | Sugioka | A61M 1/1615 210/138 |

(Continued)

FOREIGN PATENT DOCUMENTS

WO    WO-2019096598 A1 * 5/2019 ........... A61K 31/727

*Primary Examiner* — John P Go
(74) *Attorney, Agent, or Firm* — Cognition IP, P.C.; Edward Steakley; James Marc Leas

(57) ABSTRACT

A method of determining the risk of developing a known disease or condition or of identifying the presence of the known disease or condition in a subject includes obtaining subject data that includes results of blood tests. The blood tests include a basic metabolic panel (BMP) and a complete blood count (CBC) panel. The method further includes classifying the subject data with respect to the risk of the subject having or developing the known disease or condition by using the subject data in a machine learning classification system. The classification system includes a machine learning model previously trained on BMP and CBC data from a positive group of training subjects who received a diagnosis of the disease or condition and from a negative group of training subjects who were not diagnosed to have the disease or condition.

29 Claims, 15 Drawing Sheets

(56) References Cited

U.S. PATENT DOCUMENTS

| | | | |
|---|---|---|---|
| 2008/0201280 A1* | 8/2008 | Martin | G06N 20/00 |
| | | | 706/45 |
| 2011/0137852 A1* | 6/2011 | Gajic | G16H 50/20 |
| | | | 706/54 |
| 2011/0224565 A1* | 9/2011 | Ong | A61B 5/7275 |
| | | | 600/509 |
| 2012/0089421 A1* | 4/2012 | Hoffman | G16H 50/20 |
| | | | 705/3 |
| 2012/0117021 A1* | 5/2012 | Doyle | G16H 10/20 |
| | | | 706/54 |
| 2013/0027411 A1* | 1/2013 | Hebler | G16H 50/30 |
| | | | 345/501 |
| 2015/0058322 A1* | 2/2015 | Dimitrova | G16B 45/00 |
| | | | 707/722 |
| 2015/0066818 A1* | 3/2015 | Choi | G06T 7/0012 |
| | | | 706/12 |
| 2016/0239611 A1* | 8/2016 | Heldt | G16H 70/60 |
| 2018/0129911 A1* | 5/2018 | Madabhushi | G06N 3/0472 |
| 2019/0295701 A1* | 9/2019 | Das | G16H 50/70 |
| 2020/0081085 A1* | 3/2020 | Tiwari | G16H 30/40 |

\* cited by examiner

|  | RT-PCR | COVID-19 Risk Model Presumed Negative (Score<10) | COVID-19 Risk Model Inconclusive (10<Score<90) | COVID-19 Risk Model Presumed Positive (Score>90) |
|---|---|---|---|---|
| Sensitivity | 63%-71% | 93%-99% | Score value is to be used with patient signs and symptoms to guide further testing | Not Applicable |
| Specificity | 100% | Not Applicable | | 99%-100% |

FIG. 6

| Cutoff | Sensitivity (%) | Specificity (%) |
|---|---|---|
| 0 | 100 | 0 |
| 5 | 98.41 | 33.38 |
| 10 | 97.62 | 51.02 |
| 15 | 94.44 | 60.83 |
| 20 | 90.48 | 69.17 |
| 25 | 88.89 | 74.69 |
| 30 | 86.66 | 79.56 |
| 35 | 83.33 | 83.39 |
| 40 | 77.78 | 86.54 |
| 45 | 74.6 | 89.79 |
| 50 | 69.05 | 92.33 |
| 55 | 61.11 | 94.23 |
| 60 | 55.56 | 95.81 |
| 65 | 50.79 | 97.11 |
| 70 | 47.62 | 97.93 |
| 75 | 42.86 | 98.6 |
| 80 | 36.51 | 99.11 |
| 85 | 35.71 | 99.42 |
| 90 | 30.16 | 99.72 |
| 95 | 20.15 | 99.89 |
| 100 | 0.79 | 100 |

METHOD OF EARLY DETECTION, RISK STRATIFICATION, AND OUTCOMES PREDICTION OF A MEDICAL DISEASE OR CONDITION WITH MACHINE LEARNING AND ROUTINELY TAKEN PATIENT DATA

FIELD

This patent application generally relates to techniques for detection of a medical disease or condition. More particularly, it is related to techniques for detection of a medical disease or condition with machine learning and routinely taken patient data. Even more particularly it is related to techniques for establishing a risk score for a disease or condition and initiating treatment.

BACKGROUND

Improvement is needed to detect diseases or conditions without specialized tests, as well as to more rapidly and more accurately accomplish their detection and identification, and these improvements are provided in the current patent application.

SUMMARY

One aspect of the present patent application is a method of determining the risk of developing a known disease or condition or of identifying the presence of the known disease or condition in a subject. The method includes obtaining subject data that includes results of blood tests. The blood tests include a basic metabolic panel (BMP) and a complete blood count with differential (CBC w/diff) panel. The method further includes classifying the subject data with respect to the risk of the subject having or developing the known disease or condition by using the subject data in a machine learning classification system. The classification system includes a machine learning model previously trained on BMP and CBC w/diff data from a positive group of training subjects who received a diagnosis of the disease or condition and from a negative group of training subjects who were not diagnosed to have the disease or condition.

Another aspect of the present patent application is a method of determining the risk of developing a known disease or condition or of identifying presence of the known disease or condition in a subject. The method includes obtaining a single snapshot of subject data, wherein said single snapshot of subject data includes results from a single drawing of subject blood. The method further includes classifying the single snapshot of subject data with respect to the risk of the subject having or developing the known disease or condition by using the single snapshot of subject data in a machine learning classification system. The classification system includes a machine learning model previously trained on data from a positive group of training subjects who received a diagnosis of the disease or condition and from a negative group of training subjects who were not diagnosed to have the disease or condition.

BRIEF DESCRIPTION OF THE DRAWINGS

The foregoing and other aspects and advantages of the invention will be apparent from the following detailed description, as illustrated in the accompanying drawings, in which:

FIG. 6 is a chart of sensitivity and specificity of COVID-19 risk scores for potential COVID-19 patients comparing the existing standard of care, the SARS-CoV-2-PCR test, against a COVID-19 model of the present application;

FIG. 12 is a chart of showing sensitivity and specificity for different score thresholds used to generate the ROC curve for the COVID-19 model of FIG. 11;

FIG. 15 illustrates one embodiment of a graphical user interface of an app running on a smart phone, tablet, or computer that allows a user, such as a health care provider, to feed patient input data, and to receive the resulting COVID-19 risk score from application of that COVID-19 model to that input data.

DETAILED DESCRIPTION

Figure 1:
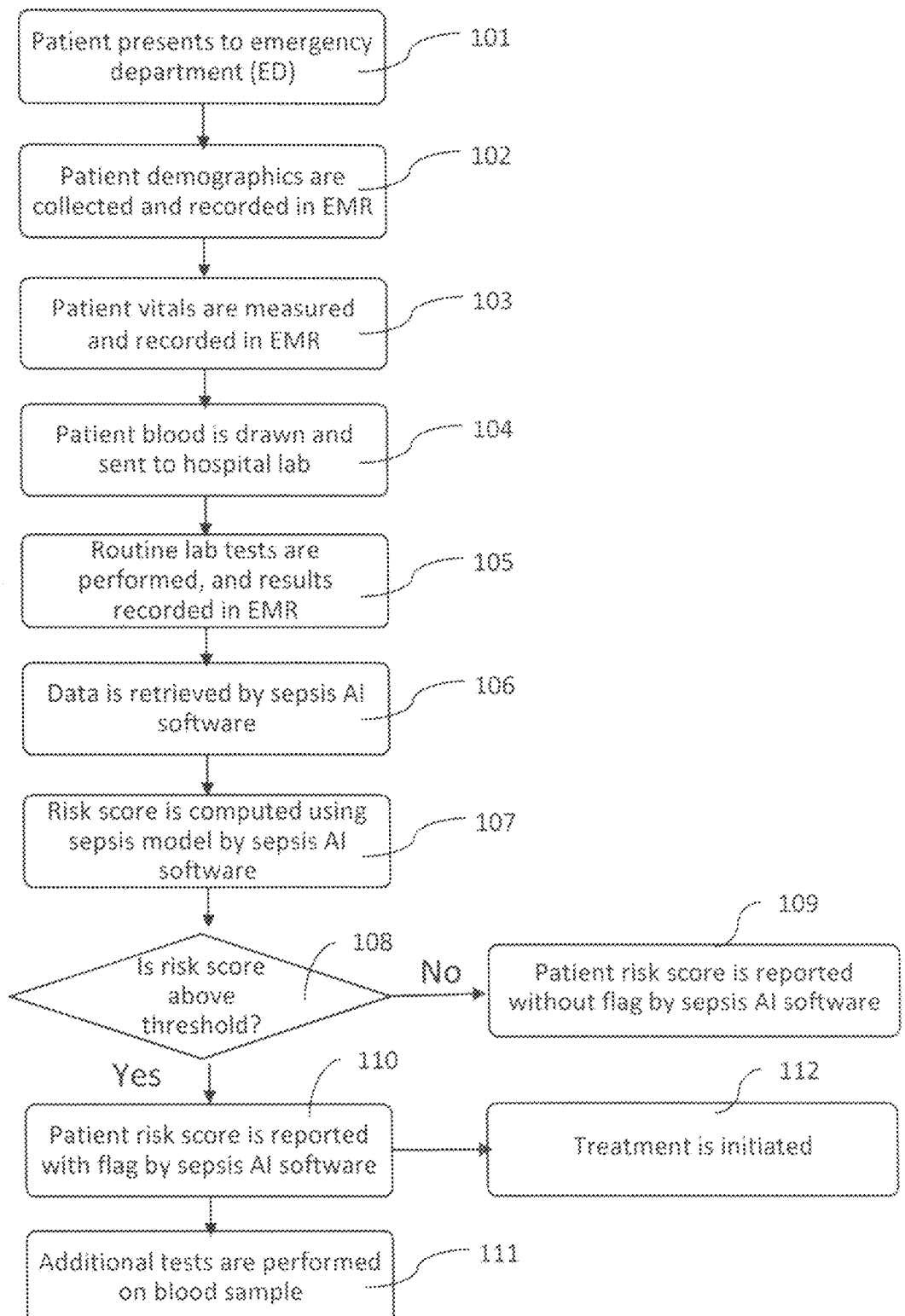
FIG. 1 is a flow chart of the process of one embodiment of the present patent application for determining a patient's risk score for sepsis based on patient demographics, vitals, and routine blood tests, as determined by software that implements the sepsis model of the present patent application, reporting the patient's sepsis risk score, highlighting the patient's sepsis risk score with a flag if it is above a threshold, and initiating treatment.

The present application provides a process to automatically screen human or animal subjects to determine those who have a high probability of having a known disease or a condition, such as sepsis and/or COVID-19, and to distinguish those who have a high probability of not having that disease or condition. In one embodiment, the screening is based on training a machine learning model with electronic medical record (EMR) data of a large number of patients, including those with the COVID-19 diagnosis and those without the COVID-19 diagnosis, and feeding the comparable data in the electronic medical record of a new patient into the machine learning model to generate a predicted score indicative of the likelihood of the presence or absence of the disease or condition in that new patient.

In one embodiment, subject data used in the machine learning model consists only of laboratory results of two blood panels, the basic metabolic panel (BMP) and the complete blood count (CBC) panel. The BMP and CBC are among the most frequently performed blood tests.

In another embodiment the subject data includes one or more additional subject data parameters in addition to the BMP and CBC subject data. Additional subject data parameters include vitals, subject demographics, urinalysis data, past medical history, medical review of systems, family history of a disease or condition, neurological assessment, chemistry determination of enzyme levels, hormone levels, and biomarkers. Additionally, quantitative metrics derived from an electrocardiogram, including presence or absence of fragmented QRS complex, heart rate variability, T peak-T end, heart rate turbulence and T wave alternans, PR interval, P-wave duration, QRS duration, RR interval, and QT interval can be included. These additional subject data parameters may be included individually or in any combination. The data for some of them may be in binary form so as to be machine readable, as for example, yes/no, regarding the presence or absence of a condition, symptom, habit, exposure, or past history or family history of a disease or condition.

Alternatively, numbers may be given to qualifiable parameters that are not quantifiable, such as occupation, past history of exposures to defined substances such as asbestos, carcinogens, and defined military exposures. Medications and known present illnesses may also be given such descriptor-numbers. Additionally locations where the subject has visited or lived in may also be given descriptor numbers. These descriptor numbers may also be modifiable by duration of exposure, such as pack-years of smoking, duration of fever in hours or days, duration of days on ventilator. The time in years or hours may be used to provide a weight with a cardinal number denoting the condition or illness or type of exposure or magnitude of exposure. All of the aforementioned descriptor-numbers may be modified by a cardinal number to represent either duration or intensity.

The process of the present patent application can also be used to automatically predict the probability of the subject developing the known disease or condition or of developing a complication of the known disease or condition, such as respiratory insufficiency requiring oxygen therapy or artificial ventilation, or the likelihood of subject death during hospitalization.

In one embodiment the score for a disease or condition is based on a single snapshot of subject data, such as results of BMP and CBC blood panels from a single drawing of subject blood. Or with vitals along with the BMP and CBC blood panels. Or with vitals, demographics, and BMP and CBC blood panels. This subject data is usually collected during a time frame when a subject first appears in an emergency department, so the screening process of the present patent application allows early knowledge of risk of a subject having or developing a disease or condition. The single snapshot of subject data may also be collected within another time frame, such as when considering discharging the subject.

In one embodiment, the information about disease risk that is automatically produced is automatically provided to the medical practitioner, preferably starting with the very first written report of test results. Such early knowledge can lead to earlier or more intensive treatment or to cessation of harmful therapy, which may prevent developing the disease or condition or reduce its severity, and improve the subject outcome.

In one experiment, the present inventors automatically generated, trained, and validated the sepsis model with a data set that included complete blood count with differential, basic metabolic panel, and vitals of 400,000 Beth Israel Deaconess Emergency Department patients stored in their electronic medical records. The model validation successfully detected sepsis with 95% accuracy (AUC).

In another experiment, described herein below, they similarly automatically generated the machine learning model for COVID-19 from BMP and CBC blood panels of emergency room patients that were stored in their electronic medical records.

To evaluate its effectiveness for identifying the risk of sepsis and COVID-19, the inventors fed each of those machine learning screening models with a single snapshot of the corresponding patient data in the electronic medical records of patients who had not been included in generating the machine learning model. Their program automatically produced diagnostic or risk probability scores for the corresponding disease or condition. They then compared the scores with the actual recorded diagnoses. The analysis showed that the screening based on the single snapshot of patient data produced diagnostic or risk probability scores that successfully identified those patients who had been diagnosed with sepsis or with COVID-19 to a high degree of accuracy.

The process is particularly suitable for emergency department use as it is based on a single snapshot of data that are currently routinely collected shortly after a patient is admitted. It is also suitable for use in an urgent care facility, an intensive care unit (ICU), a medical provider's office, or in any other location where laboratory services are ordered. A diagnosis or prognosis identified by the screening may be immediately confirmed with additional tests, either on the blood already drawn or by obtaining a new sample of blood, if necessary.

In one embodiment, the screening process is run each time vitals and blood panel tests are collected for a patient, such as during the course of treatment, providing scores that confirm or revise an earlier diagnosis or that evaluate the success or failure of a treatment.

In the case in which patient data is taken at documented times the interval between individual vitals tests or between samples of blood taken may be used to determine the rate of change of the parameters reported for a given measurement. The machine learning method may make use of the time rate of change of a parameter—the parameter's velocity. It may also make use of the rate that velocity is changing with time. It may make use of the velocity of multiple parameters and the rates they each change.

The vitals parameters used by the present applicants for the COVID-19 and sepsis machine learning methods included systolic and diastolic blood pressure, pulse, temperature, oxygen saturation level, and respiration rate, typically all taken in one period of time, such as during the time shortly after a patient enters the emergency department. The blood panels included the basic metabolic panel (BMP) and the complete blood count (CBC) panel. The demographics used for sepsis in the experiment they performed included age, race, and sex. Additional demographics may be included, including location of residence, occupational history, and other machine readable demographic information.

In the experiments run by the present inventors, a machine learning program based on the Python library scikit-learn with the classifier XGBClassifier was trained and used to generate COVID-19 risk scores based on vitals and BMP and CBC panels. Separately, the same machine learning program was trained and used to generate sepsis scores based on vitals, demographics, and BMP and CBC panels. While the inventors used a specific library and classifier for this task, various other machine learning software packages can be used, including but not limited to RapidMiner, KNIME, Weka, Apache Mahout, mlpy, OpenCV, Orange, Shogun toolbox, ODM, LIONsolver, Google Prediction API, and MCMLL.

In another embodiment, in addition to the six vitals listed herein above, vitals parameters may also include such other routinely taken ones as height and weight. In addition to age, sex, and race, the demographic parameters may also include geographic location, occupation, and yes/no answers to smoking history and alcohol and drug use, as well as answers to medications used prior to admission.

The machine learning screening process can also be used to screen subjects for the presence or risk of developing other diseases or conditions, such as pulmonary embolism, diabetic keto-acidosis, pyelonephritis, congestive heart failure, dehydration, syndrome of inappropriate antidiuretic hormone (ADH), renal insufficiency, pneumonia, myocardial infarction and hematological conditions, such as anemia of all causes, as well as blood dyscrasias. A machine learning model may similarly be generated from the BMP and CBC subject data that is stored in electronic medical records. The machine learning model may also include any of the above listed additional subject data parameters. Once a machine learning model is generated for each disease or condition from the data in the electronic medical records, the corresponding subject data from each subsequently tested human or animal subject is then automatically fed into the machine learning model for each of the diseases or conditions to produce a probability score of a diagnosis or outcome for that disease or condition. A patient may thus be automatically evaluated for multiple diseases or conditions based on the corresponding subject data. Results may be displayed to the practitioner with those diseases or conditions with high scores highlighted.

Dipstick urine analysis test parameters that may be included in the machine learning model include pH, Albumin, Glucose, Ketones, Bilirubin, Blood, Nitrite, Urobilinogen, Specific gravity, and Leukocyte esterase. For certain diseases and conditions, a deviation from a normal value of one or more individual parameters in urinalysis data has been sufficient for a highly trained practitioner to accurately diagnose a disease or condition, such as diabetes melitus, diabetic ketosis, urinary infection, chronic renal disease, hepatitis, biliary obstruction, hemolytic anemia, dehydration, hematuria associated with any urinary system tumor, and renal lithiasis and or colic due to kidney stone. When the data from the urine dipstick is combined with blood panel data, such a highly trained practitioner could often also diagnose diseases or conditions, such as metabolic acidosis, uremia, nephrotic syndrome, syndrome of inappropriate ADH, dehydration, pyelonephritis, hepatitis, diabetes insipidus, renal tubular acidosis, and glomerulonephritis. But even in the aforementioned cases the machine learning screening based on the combination of routinely taken patient data likely will improve diagnostic accuracy and confidence. In other cases, such as sepsis or risk of COVID-19, no individual routinely-collected parameter or set of routinely collected parameters has been sufficient for a highly trained practitioner to diagnose with high sensitivity and specificity as the present inventors showed can be achieved by feeding the vitals, BMP, and CBC subject data into the machine learning model generated as described herein. Addition of urine analysis to the machine learning may improve sensitivity and specificity for these diseases or conditions.

In another embodiment, the inventors found that overall accuracy of the model was comparable relying only on the routine BMP and CBC blood tests without including subject vitals in the subject data provided for machine learning. However, applicants found that they do get better results for COVID-19 with an expanded set of blood tests, such as the Comprehensive Metabolic Panel (CMP) and CBC with differential (CBC w/diff). The CMP includes both the BMP and the Liver Function Test (LFT) panel. The CBC with differential categorizes and counts the different types of white blood cells present in a sample of blood, including neutrophils, monocytes, lymphocytes, eosinophils, and basophils.

Inclusion of medical history and medical review of systems in a machine readable form, can be by way of yes/no answers to a list of symptoms, diseases, conditions, and previous procedures. For consideration of COVID-19, for example, a medical review of systems that may be included in the machine learning method may include the patient's yes/no answers to questions about whether the patient had experienced symptoms, such as shortness of breath, chills, rigors, headaches, confusion, loss of sensation of taste or smell or chest pain.

The machine learning model may also include such additional subject data parameters as enzyme levels, such as amylase and lipase levels, which when elevated are indicative of pancreatitis. It may also include biomarkers, such as beta naturetic peptide (BNP), troponin, D-Dimer, and traumatic brain injury (TBI) markers. It may also include organ specific tests indicative of neoplasia, such as prostate specific antigen (PSA), carcinoembryonic antigen (CEA) test, and the CA 125 test for ovarian cancer. It may also include tests for cardiac, pulmonary, coagulation, and pancreatic illnesses. It may also include tests results for drug levels, generally performed in a toxicology lab. Toxicology levels may be used to determine levels of both drugs of abuse and therapeutic drugs prescribed by a physician to determine if a patient is overdosed.

The inclusion of the additional subject data parameters in the machine learning model and in the patient data fed into the machine learning model may further improve the ability of the machine learning method to automatically score a diagnosis and to determine the risk of developing the disease or condition both for diseases where the diagnosis could be ascertained by a highly trained physician and for conditions where even a highly trained physician could not make an accurate diagnosis. The additional subject data parameters included in the machine learning model and in the patient data fed into the machine learning model may be periodically updated to include new laboratory tests as medical science progresses and as diagnostic ability of medical practitioners increases.

In another embodiment, the present inventors recognized that a particular score based on vitals, BMP, and CBC and, optionally one or more of the additional subject data parameters could provide grounds for an order to perform one or more additional tests. The additional test may be automatically ordered in view of results provided by the machine learning model. Alternatively, the order to perform the additional test could be left to the discretion of the medical provider. The additional test may be performed on an already taken blood or urine sample or on a newly procured sample to further confirm or deny the machine-generated diagnosis score. In one embodiment, the patient data obtained with that test is included with other patient data and analyzed in the machine learning model for recalculation of the score.

In one embodiment, the present inventors found that a score greater than 90 provides a presumptive positive diagnosis and a score less than 10 provides a presumptive negative diagnosis. Patient scores between 10 and 90 may provide informative guidance on supplementary diagnostic testing.

Not all the blood tests listed below in the BMP and CBC panels figured prominently in the machine learning model developed by the present inventors. While data for all these blood tests were included in the data the present inventors provided for machine learning, in the resulting model several of these tests had low to negligible weight. The specific routinely-collected data that strongly and weakly influenced the machine learning model varied for the different diseases or conditions, such as COVID-19 and sepsis, that have so far been reduced to practice under the method of the present patent application.

In addition, noteworthy is that the set of tests that comprise each routinely-taken blood test panel may vary between laboratories. For instance, band neutrophils (% or absolute count) were not in our experimental CBC panel but are included in Cigna's version. The AACC version of BMP includes calcium while other versions may not. Commonality between the tests used for machine learning training and those included in the subject data for each presenting patient can be obtained by rerunning the machine learning electronic medical record data to update the machine learning model to include the corresponding subject data.

One embodiment of a Basic Metabolic Panel (BMP) includes:
Creatinine
Urea Nitrogen
Sodium
Chloride
Potassium
Bicarbonate
Glucose
Anion Gap
Calcium One embodiment of a Complete Blood Count (CBC) with differential includes:
White Blood Cell Count
Red Blood Cell Count
Hematocrit
Hemoglobin
RDW (Red Cell Distribution Width)
MCH (Mean Corpuscular Hemoglobin)
MCHC (Mean Corpuscular Hemoglobin Concentration)
MCV (Mean Corpuscular Volume)
Platelet Count
Eosinophils (% or absolute count)
Lymphocytes (% or absolute count)
Monocytes (% or absolute count)
Neutrophils (% or absolute count)
Basophils (% or absolute count)

One embodiment of a Liver Function Panel (LFP) includes:
Alanine Aminotransferase (ALT)
Albumin
Alkaline Phosphatase
Asparate Aminotransferase (AST)
Bilirubin
Protein, Total The present patent application provides a way to screen all patients for risk of having or developing a known disease or condition, such as COVID-19 or sepsis, based on just the blood panels or on the vitals and the blood panels with or without additional subject data parameters. The score for disease risk automatically produced by the method is provided to the practitioner, preferably starting with the very first report of blood test results. The score may be updated with each successive collection of subject data.

The information about disease or condition risk may thus even be provided to the practitioner in cases before he or she has seen the patient. The present inventors recognized that basing the screening on routinely taken parameters, such as BMP and CBC blood panels, is advantageous because this data is often obtained promptly upon the patient entering the emergency department. Using this data is also advantageous because it is widely available in electronic medical records for training the machine learning model. Also, as physicians don't ordinarily order other more specific tests without first forming a reasonable suspicion of a specific disease or condition, the present patent application provides a screening score for each disease or condition or risk of the disease or condition to physicians without requiring them to modify their existing workflow or have reason to suspect that the problem is developing. Thus, for example risk of COVID-19 or sepsis or another known disease or condition is automatically reported very soon after the patient arrives in the emergency department, and if a threshold score is defined, as further described herein below, the probability score generated by the machine learning model may be highlighted in the report.

In one aspect of the method, a patient presents to the emergency department of a hospital for any reason for which vitals, BMP, and CBC data is collected, as shown in box 101 of the flow chart of FIG. 1. Hospital personnel collect and record patient demographics in the patient's electronic medical record, as shown in box 102. Medical personnel measure and record patient vitals in the patient's electronic medical record, draw a sample of the patient's blood, and send the sample to the lab, as shown in boxes 103 and 104. The lab performs the BMP and CBC panels on the sample and stores the results in the patient's electronic medical record, as shown in box 105. Running on a processor in the cloud, the known disease or condition Artificial Intelligence (AI) software retrieves the snapshot of patient data, including the routinely taken patient vitals and blood panels data from the electronic medical record, and may also include patient demographics, urine analysis data, enzyme and marker levels, medical history and medical review of systems data, as shown in box 106, and applies the known disease or condition model to compute the risk score for that known disease or condition, as shown in box 107. Thus, the risk of the patient having a disease, such as COVID-19 or a condition, such as sepsis, is identified and presented to the practitioner along with the vitals, BMP, and CBC subject data. The AI software can also run on a local computer.

In another embodiment, the patient data is directly transferred to the AI software as test results become available before entry in the patient's medical record.

In decision diamond 108, the processor determines whether or not the score for the known disease or condition is above a preset threshold. In either case the score is reported to the physician but if not above the threshold, the score is reported without a highlighting flag, as shown in box 109. If the score is above the threshold, the report to the physician includes a highlighting flag, as shown in box 110 for that disease or condition. In addition, if the score is above the threshold, a further test on the blood sample may be run, as shown in box 111 and/or treatment initiated, as shown in box 112.

Figure 2:
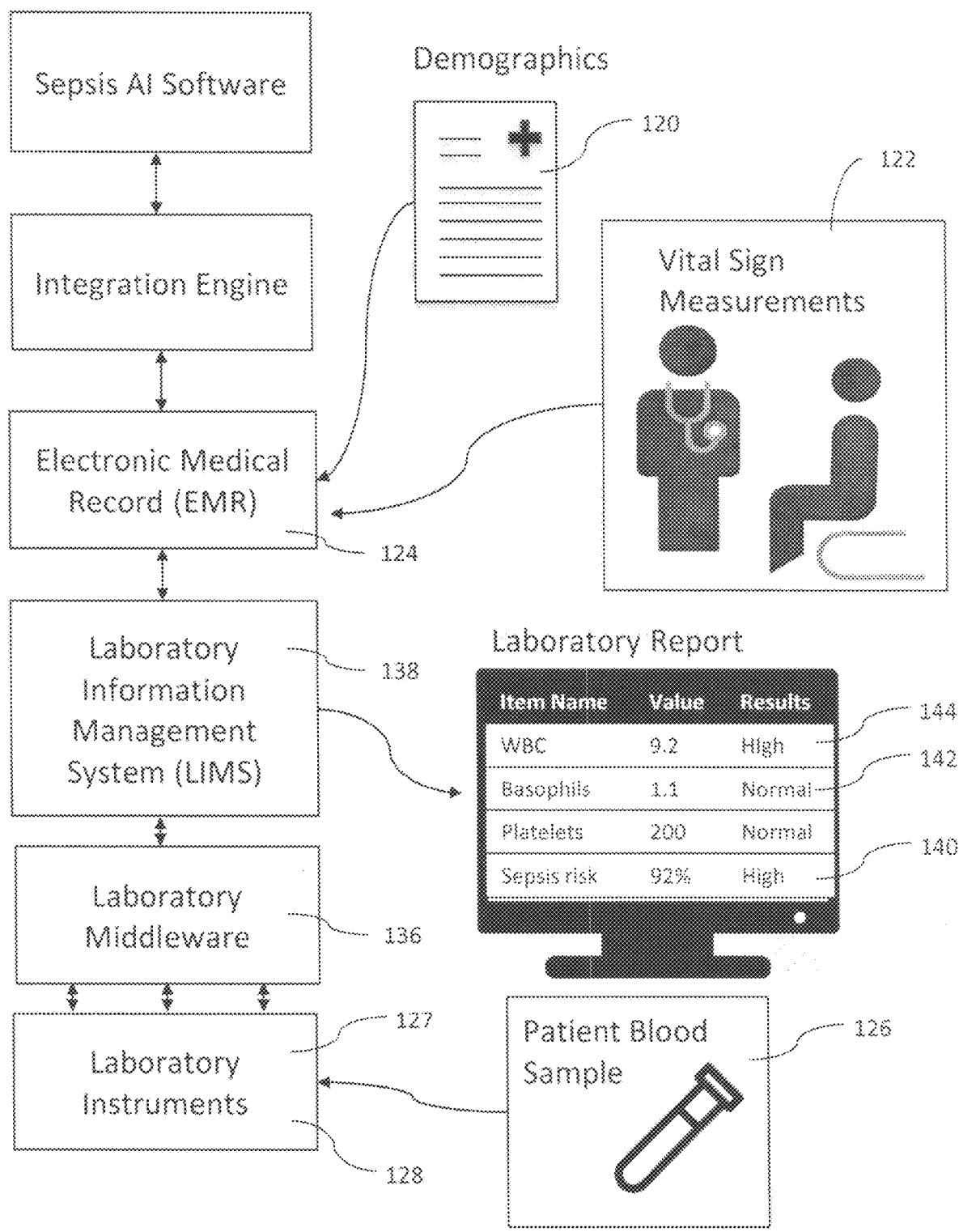
FIG. 2 is a block diagram showing one embodiment of hardware and software components of the present patent application, the patient demographics, vitals, and routine blood test inputs, and the laboratory report output, including the sepsis risk score.

The block diagram in FIG. 2 further illustrates patient demographics 120 and vital signs data 122 provided to electronic medical record 124 while a patient blood sample 126 is provided to the lab, routine blood panels measured with lab instruments 127 to provide blood panel data 128, which is processed with lab middleware 136 and with lab information management system 138, and stored in the patient's electronic medical record 124. When the patient data, such as, for sepsis, including patient demographics 120, vital signs data 122, and blood panel data 128, has been collected and is available, lab information management system 138 uses the AI software and calculates disease or condition risk score 140 with the machine learning model and runs laboratory report 142 that also includes blood panel results 144 and disease or condition score 140.

The blood panels may be performed on a sample of subject blood that is be taken from the subject around the same time as the vitals were taken.

In the machine learning process used by the present inventors, snapshots of patient vitals, blood panel parameters, and patient demographics stored in the electronic medical records (EMR) of thousands of patients who either did develop or did not develop a specific disease or condition were used to train the machine learning model. The training was performed with the XGBClassifier model in scikit-learn, and validated using 5-fold cross-validation. In order to make predictions based on the patient data, the trained model was saved to a file and used with scikit-learn. Other software that is able to import trained machine learning models to make predictions, can be used, including Google AI Platform, Amazon ML, and others.

Figure 3:
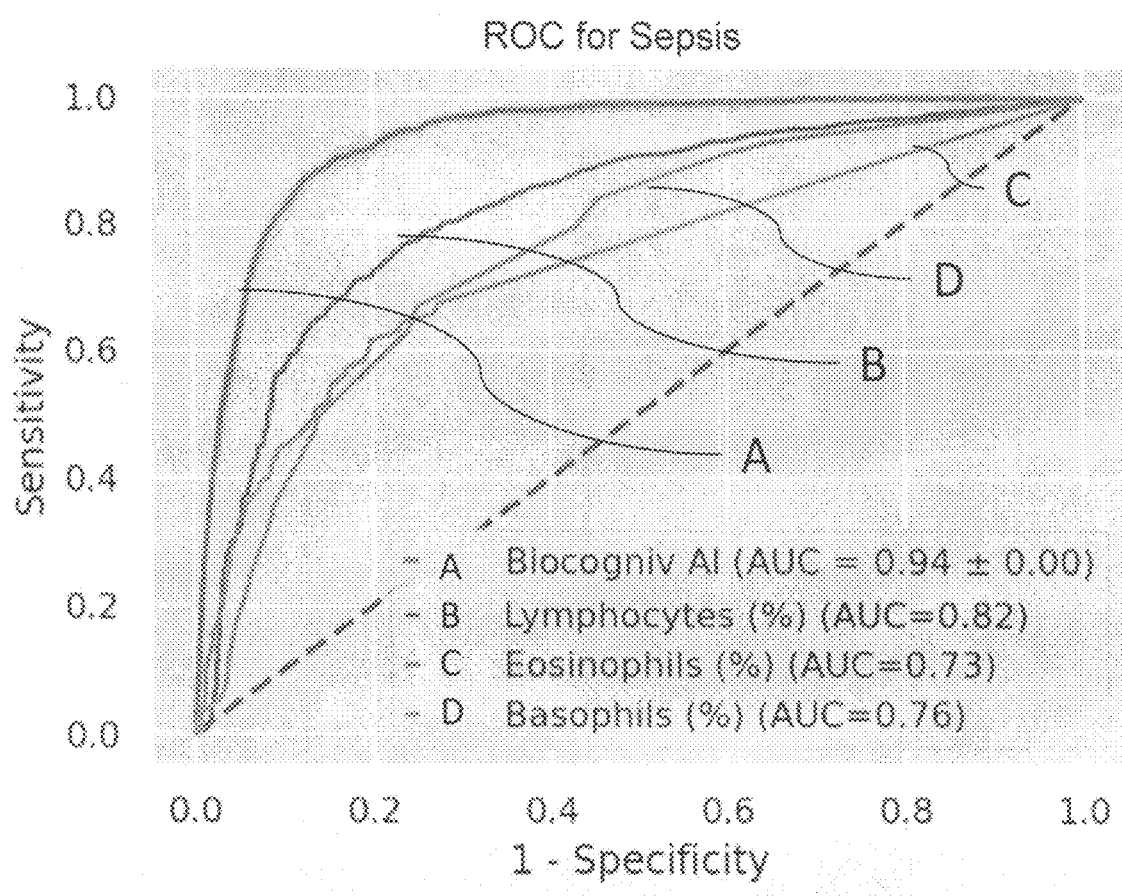
FIG. 3 is a chart comparing the receiver operating characteristic (ROC) curve for a sepsis model created by applying the machine learning technique of the present patent application with the ROC curves for the three most predictive individual blood tests that were included as input data in the model.

The presence or absence of the specific disease or condition in the training population was determined from standardized diagnostic codes in the electronic medical record. That shaped model was then tested, in a validation step, on medical record data to which the training model had not yet been exposed. This model development and validation was repeated five times, each time dividing the dataset differently between four parts training data and one-part validation data (a 5-fold cross validation). Afterwards the best machine learning model was chosen and found to have an Area Under the Receiver Operating Characteristics (ROC) Curve (AUC) of 0.94, as shown curve A of FIG. 3. Also shown are individual curves for three of the top input features for the sepsis model, Basophils curve D, Eosinophils curve C, and lymphocytes curve B.

Machine learning enables decision-making based on a combination of vitals and BMP and CBC blood panel parameters, with the appropriate weighting determined by the training. Demographics, urine analysis data, blood chemical analyses, enzyme and marker levels, medical history and medical review of systems data may also be included in the combination fed into the machine learning model. The present inventors found from the machine learning, for example, that cell differential counts, like Lymphocytes, and metabolic levels, like chloride and bicarbonate, have some effect on a patient's likelihood of developing sepsis. They also found that these, and other parameters of the blood panels, previously not considered as sepsis indicators, can be included, as determined during the machine learning, in combination with all the other parameters, in the screening of a new subject sample.

In one embodiment the machine learning model includes ensemble classification methods like random forests and gradient boosting. In another embodiment it includes other supervised learning methods like support vector machines and neural networks. Machine learning systems included classification and regression trees, decision trees, and a gradient boosting model.

Figure 4:
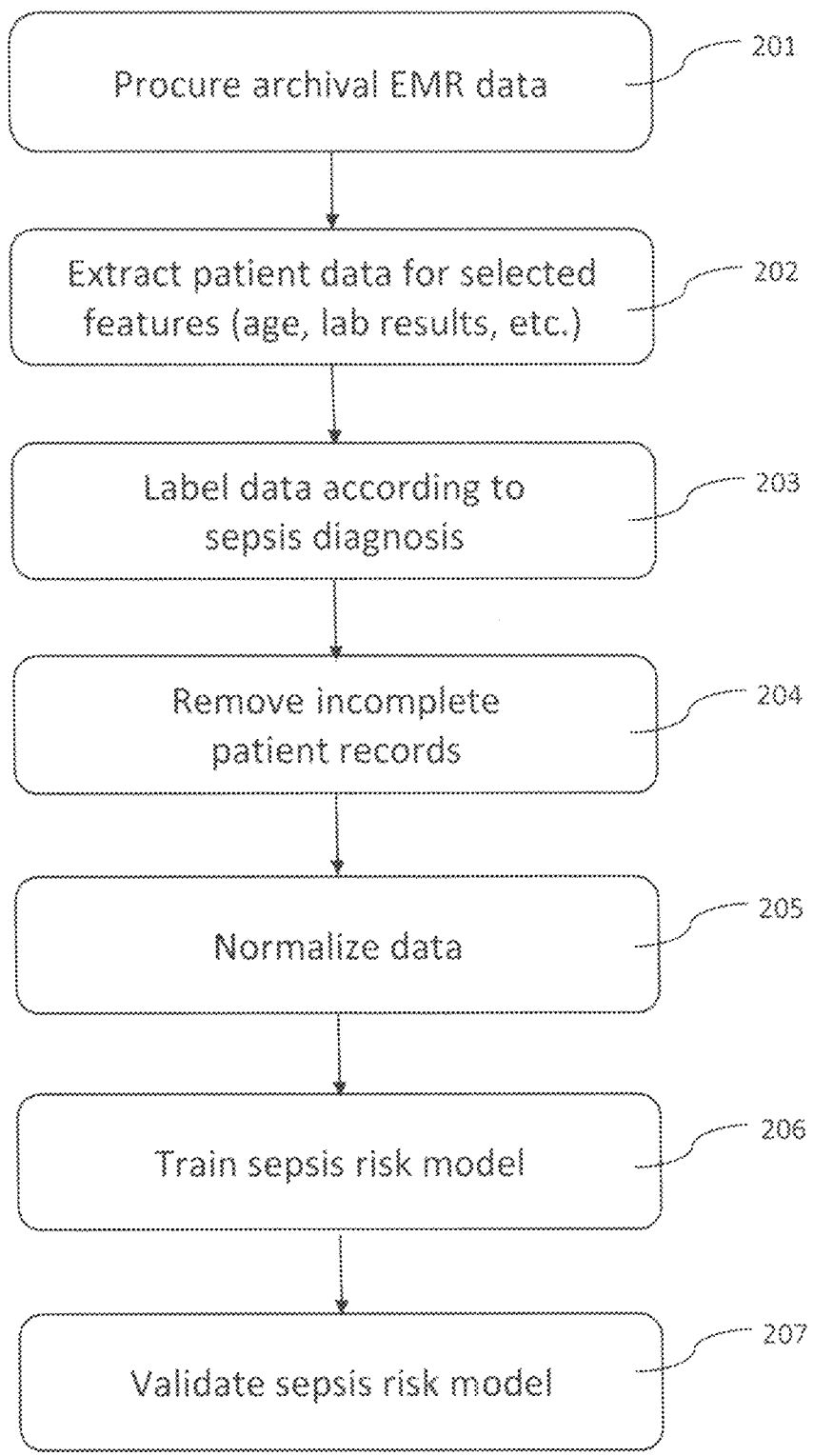
FIG. 4 is a flow chart of the process of one embodiment of the present patent application for training the sepsis model and validating the sepsis model.

In the machine learning process for sepsis that the present applicants used, archival electronic medical record data was procured for machine learning training, as shown in box 201 of FIG. 4. For the sepsis work, patient demographics, vitals, and blood panels data was extracted from the electronic medical record data for hundreds or thousands of patients, as shown in box 202, and data for each of the patients was labeled according to whether that patient received a sepsis diagnosis at some point in their treatment, as shown in box 203. A patient data that was incomplete was not included in the machine learning training, as shown in box 204. Any normalization of the data (such as conversion of laboratory units) is performed, as shown in box 205. Calibration of the model may also be performed using calibration functions in the machine learning library, for example the scikit-learn Python library. The machine learning model was then trained with most of the archival data to provide the sepsis model, as shown in box 206 and the model was validated with unused ("holdout") archival data, as shown in box 207.

In one embodiment, electronic medical record data is extracted from the electronic medical record from one or more hospitals, transformed into common formats and naming conventions such that data from different sources can be directly compared, and loaded into a database. Data from the database is selected according to eligibility criteria and assembled into a table and then used in the machine learning.

In another embodiment, data that hospital staff has collected from selected patients is entered into a table in a spreadsheet.

In one embodiment, a sepsis risk score was calculated. The sepsis risk score is related to the probability of the subject having or developing sepsis. In use, in one embodiment, the sepsis risk score is included in the report to the practitioner considering the subject blood panel results.

Figure 5:
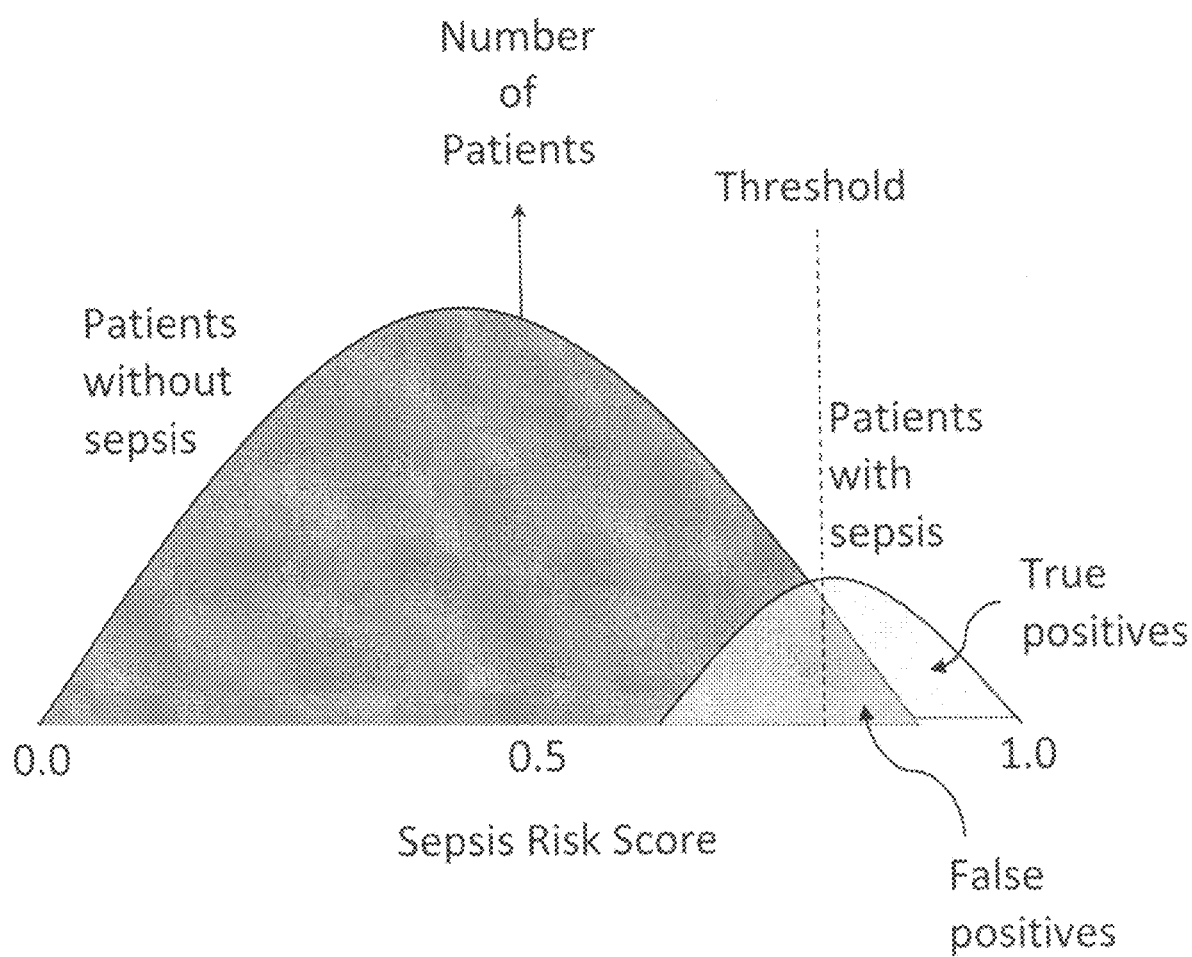
FIG. 5 is a graph showing how a sepsis risk score differs for patients without sepsis, patients with sepsis, the threshold used, and the true and false positives.

As with any imperfect diagnostic method, when the sepsis model was applied to calculate sepsis risk score for a group of patients who were known to either have sepsis or to not have sepsis, the true positive and true negative populations overlapped, as shown in FIG. 5. A score showing no such overlap would be a perfect classifier of the condition (i.e. 100% accurate). A sepsis risk score threshold is thus set to separate the patients into two groups: lower risk patients requiring less clinical consideration for sepsis, and higher risk patients requiring more clinical consideration for sepsis. The threshold provides a sepsis score level above which further consideration or action by a medical provider is called for. Any score above this threshold score is highlighted to the doctor, such as in red on the blood panel report, if the subject has a sepsis score above the threshold score.

In the example of FIG. 5, the prevalence of sepsis among patients presenting to a hospital emergency department is about 10%, so the number of patients without a high risk of sepsis is about 10 times larger than the number of patients with a high risk. To use the machine learning model to particularly identify patients who have a high risk of developing sepsis, without including in that group a large number of patients who do not have a high risk, which could lead to clinician "alert fatigue," the threshold may be set as shown in FIG. 5, so substantially more patients with a high risk are highlighted to the doctor as have a score above the threshold than are patients with a lower risk. In one embodiment, the threshold is automatically set in the program according to such a criterion. In another embodiment, the threshold is adjustable by clinicians and the setting they select input into the program.

For example, the threshold score may be chosen as the score at which twice as many subjects with a score higher than the threshold score are likely to have at least early-stage sepsis as subjects who are free of sepsis. Alternatively a threshold score may be chosen as the score at which 90% of subjects with a score that is higher than the threshold score are likely to have at least early-stage sepsis. Or it may be chosen so that a subject with a score lower than the the threshold score has a 95% chance of not having the disease or condition. Or so that the negative predictive value of the test is 0.99 based on the prevalence of the disease or condition among the group of subjects to which the test is being applied. Or so that the positive predictive value of the test is 0.99 based on the prevalence of the disease or condition among the group of subjects to which the test is being applied Recognizing sepsis early is important for the timely treatments that have been shown to improve outcomes. Sepsis generally begins as a systemic inflammatory response to an infection, and about 25% of patients progress to advanced stages, which entail organ failure and septic shock, and these may occur within just over one day. The present patent application allows predicting the risk of sepsis before it manifests so it can be averted.

Other outcomes that the present patent application can be used to predict include recovery, in-hospital death, and mortality within 48 hours. It can also be used to predict the level of care needed for a subject, such as admission to hospital, need for respirator, likelihood of need intubation, likelihood of need for intensive care unit (ICU), expected length of stay in hospital, and likelihood of discharge from hospital. As treatment is provided the scheme of the present patent application can be repeated to determine whether the predicted level of care changes, to monitor disease progression, and to gauge effectiveness of treatment.

In one embodiment, automatic action is provided if the subject has a score above the threshold score. For example, in response to any sepsis risk score above threshold, at least one further non-routine test on the sample of subject blood is performed to further evaluate the patient's risk for developing sepsis. The further non-routine test may include a lactate test and/or a procalcitonin test. Emergency department personnel may automatically establish that the further non-routine test or tests are automatically ordered for any subject with a sepsis risk score above the threshold.

A practitioner may also consider starting treatment to prevent sepsis from developing in a subject who presents with a sepsis risk score above the threshold score. The treatment options for sepsis include providing antibiotics, antiviral medication, antifungal medication, intravenous fluids, oxygen tube, a face mask, or mechanical ventilation, transfusion, a steroid, vasopressor medication, or surgery. For COVID-19 treatment options include providing antibiotics, antiviral medication, monoclonal antibodies, an anticoagulant, a steroid, an immunosuppressant, vasopressor medication, convalescent plasma, intravenous fluids, high flow nasal cannula, mechanical ventilation, non-invasive ventilation, transfusion, or self-proning oxygenation.

As sepsis is a frequent complication of the novel coronavirus, use of the sepsis screen of the present patent application is particularly valuable in their care and treatment. Recognizing that the coronavirus pandemic may significantly change the pretest population used for training the model, several choices are available for training. (1) Using the sepsis score as-is for COVID-19 patients, i.e. using the model as trained on a population without the COVID-19; (2) Retrain the model with COVID-19 patients included in the overall population; and (3) Retrain the model with only definite-positive and definite-negative COVID-19 patients.

Applicants found that the system of the present patent application for COVID-19 diagnostics, called AI-COVID, can provide diagnostic scores in less than one hour (and in many hospitals, in under 30 minutes) using only vitals and routine blood tests that are almost always ordered for patients with respiratory symptoms. The HIPAA-compliant application automatically collects the necessary data from the hospital's electronic medical record system for the patient and returns the score back to the physician via the electronic medical record.

In one experiment, a COVID-19 model was trained and independently validated on a total of more than 6,000 emergency department patient encounters at over 200 US hospitals. The positives come from 126 RT-PCR-confirmed COVID-19 cases from three healthcare facilities, namely Cedars-Sinai (Hollywood, Calif.), the University of Vermont Medical Center (UVMMC, Burlington, Vt.), and Maimonides Medical Center (Brooklyn, N.Y.). The data from UVMMC and Cedars-Sinai were obtained directly through Institutional Review Board (IRB)-cleared collaborations, whereas the data from Maimonides was obtained through publicly available records.

When cross-validated in this multicenter, real world evidence study that included electronic medical records from 126 COVID-19 positive patients from 3 geographically distinct emergency departments and ~6,000 negative patients from another 200+ emergency departments, the COVID-19 model classified patients into presumptive negative and positive with 97.6% sensitivity [95% CI: 93.2%-99.5%] and 99.7% specificity [95% CI: 99.5%-99.8%].

These results are shown in tabular form in FIG. 6, which compares performance of this COVID-19 model against the existing standard of care in the emergency department (ED). PCR sensitivities are from clinical practice using nasopharyngeal swabs, which include effects of stage-dependent viral load, specimen collection, patience tolerance, and others that are not traditionally accounted for in manufacturer-reported (in vitro) numbers. PCR specificity is presumed specificity, since a positive PCR is considered the "gold standard" in most COVID-19 studies.

Figure 7A:
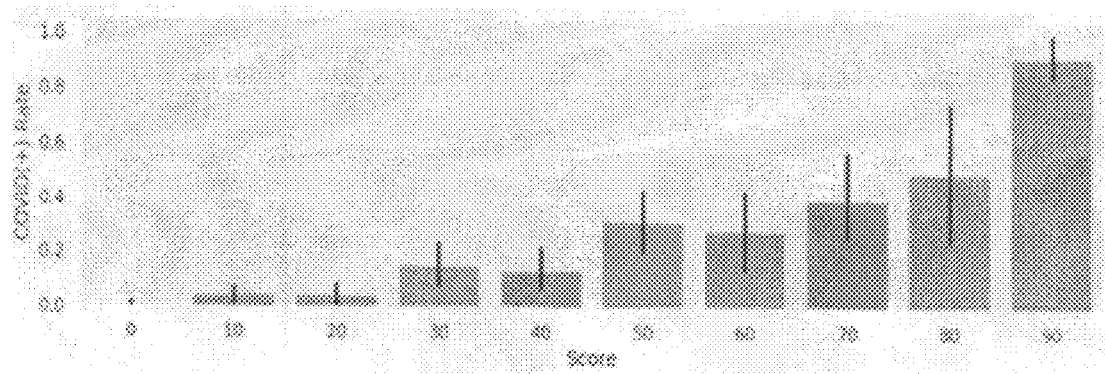
FIG. 7A is a histogram showing the correlation of observed frequency of subjects that are positive for COVID-19 (based on PCR testing) with the COVID-19 risk score group.
Figure 7B:
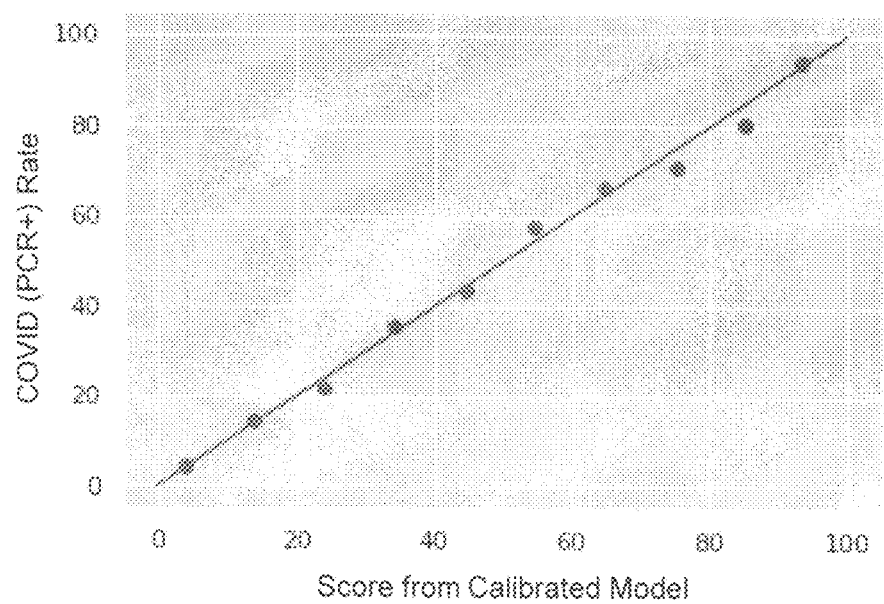
FIG. 7B is a graph showing the COVID-19 positive rate as determined by the PCR test v. the score determined from the calibrated model.

The COVID-19 model generates a score from 0-100 that is seen to be proportional to the likelihood that the patient is COVID-19 positive (see FIGS. 7a and 7b). The subject data divided into 10 decile groups, according to subject scores, and the number of COVID-19 PCR (+) subjects in each decile group was counted. That number of COVID-19 PCR (+) subjects was divided by the number of subjects the model provides in that decile and plotted as a histogram with each of the 10 decile groups, as shown in FIG. 7a. While in FIG. 7a as the model prediction probability increases, the COVID-19 PCR (+) rate also increases. However, the histogram does not show a tight linear relationship.

In another experiment, the model was calibrated with and calibration transform function called "CalibratedClassifierCV" that is available in the scikit-learn Python library. After this calibration the observed rate of COVID-19 in each decile predicted by the model more closely matched the PCR COVID-19(+) rate, as shown in FIG. 7b. Thus, the relation between observed PCR COVID-19(+) rate and the predicted risk of COVID-19 as determined by the calibrated COVID-19 model was seen to be substantially linear.

In one embodiment the COVID-19 model is deployed as a secure cloud service that connects remotely to the hospital via secure virtual private network (VPN). The existing digital and laboratory infrastructure of the hospital may be used. As all testing is routine, no new instrument or reagent is required at the hospital. Only the common equipment and reagents used for analyzing BMP and CBC are used. Once deployed at a hospital system, the service provides results to the physician as soon as the laboratory results are available in the Electronic Medical Record (EMR) system. As emergency department laboratory tests are typically urgent (STAT) orders, therefore a diagnostic result will typically be available in less than one hour. A schematic of the product flow is shown in FIG. 8.

Figure 8:
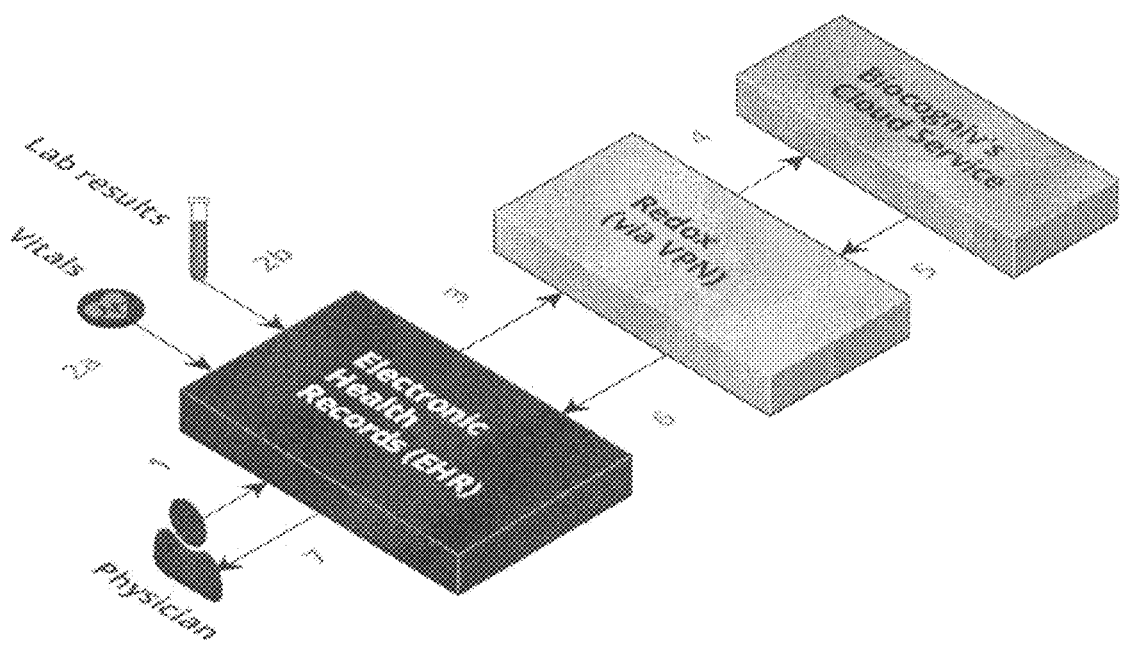
FIG. 8 is a block diagram showing the flow of information for one embodiment of a cloud-based system of the present patent application.

In use, an Emergency Department physician places orders for BMP and CBC lab tests if they are not routinely performed, as shown in step 1 of FIG. 8. Patient vitals and lab results are recorded in the patient's electronic medical record (EMR), as shown in step 2. The hospital EMR software sends patient lab results to a software intermediary, such as Redox, that enables communication between a hospital EMR and external software via a secure Virtual Private Network, as shown in step 3. Redox notifies a cloud service containing the COVID-19 model, such as Biocogniv's Cloud Service, of data availability via a secure HTTP website, as shown in step 4, which presents the data to the COVID-19 model. The COVID-19 model uses the patient data to generate a COVID risk score and sends the score back to Redox via secure HTTP, as shown in step 5. Redox then forwards the risk score back to the EMR as an additional "virtual" laboratory test result via secure VPN, as shown in step 6. Emergency Department providers are then able to see the risk score at the same time—and on the same screen—as the ordered laboratory results, as shown in step 7. Alternatively, the software with the COVID-19 model could be located on a hospital computer and communicate directly with the hospital medical record software.

One result of using data from a large number of hospitals facilities, such as urban. rural, small, large, academic teaching centers, and community hospitals for training and validation is wide diversity, such that data from a subject in a new hospital within the geographic area of the hospitals used for training can be classified by the machine learning algorithm without having to train and validate again.

In one embodiment the model is trained using data representative of the population that the resulting test will be applied to. For example, a model that is to be used across the continental US may include data from hospitals spread out across that geographic area so care practices, climate, patient race and other variables that may impact health conditions and diseases are included.

Data from a hospital that provides its laboratory test results using different laboratory units is converted to a common set of units. The machine learning algorithm is adjusted so it works in different care settings and for different demographic populations, including gender, age, and racial and ethnic groups. New data from a diverse set of healthcare facilities is periodically run to update the model.

In one experiment, described in the paper, "Development and External Validation of a Machine Learning Tool to Rule Out COVID-19 Among Adults in the Emergency Department Using Routine Blood Tests: A Large, Multicenter, Real-World Study," by Timothy B Plante, et al, *J Med Internet Res* 2020; 22(12):e24048, the eligible patients for inclusion in the training groups were adults more than 20 years old and in an emergency department at one of the included hospitals during either the prepandemic time frame or the pandemic time frame. Standard diagnostic and procedural codes can be used to determine patient eligibility for inclusion or exclusion from machine learning training groups. In this experiment, patients were excluded from the training groups if they were missing a laboratory result included in the model on the day of presentation to the emergency department or if any of their laboratory results were reported with inappropriate units or incorrect specimen type. Patients were defined as PCR-positive for COVID-19 (hereafter, PCR-positive) if they had a positive SARS-CoV-2-RNA test on the day of presentation to the emergency department.

In one embodiment, the model is trained and validated on similar types of data. A model that is trained and validated on data having a common set of patient selection criteria might later be validated on another set of data that has a different set of patient selection criteria. For example, a model for COVID-19 trained and validated on data from adult emergency department patients, may later be validated on data from children.

In one embodiment, the model estimates COVID-19 status of a patient on the day the patient presents to an emergency department using common laboratory tests collected that day. In one experiment, model training began with results of the 29 routinely measured blood test or features in the CMP and the CBC with differential. In many cases the differential is automatically included in the CBC, but it does depend on what blood count equipment is available in a particular hospital lab.

In one experiment, recursive feature elimination with cross-validation (RFECV) was performed to determine a reduced set of blood tests. RFECV is an algorithm that is implemented in the Sci-Kit Learn library that enables feature reduction. The model is iteratively trained on different sets of features and model performance is calculated for each input set. Features that do not improve the model performance are eliminated. In this experiment, the gradient boosting model as implemented in XGBoost was used. The 29 blood tests of the BMP, CBC, and FLT were the features used in the gradient boosting model and the AUC metric was used in the calculation. They found that just 15 of those 29 blood test results played a significant role in the scoring, as listed herein below.

No nasopharyngeal RT-PCR negatives were included in training data set in view of the questionable sensitivity of this test. Instead, in the experiment the present inventors collected approximately 6,000 negative controls from emergency department patients diagnosed with various respiratory conditions (pneumonia, influenza, bronchitis, etc) at more than 200 US hospitals from time periods before the COVID-19 pandemic started, including more than 4,000 from Beth Israel Deaconess Medical Center (BIDMC, Boston, Mass., 2008-2018) and approximately 2,300 from the public dataset called "eICU" that includes data collected during the 2014-2015 time frame from more than 200 hospitals.

The result of the model is a score, from 0-100, indicating the likelihood of the patient being positive for COVID-19.

Figure 9:
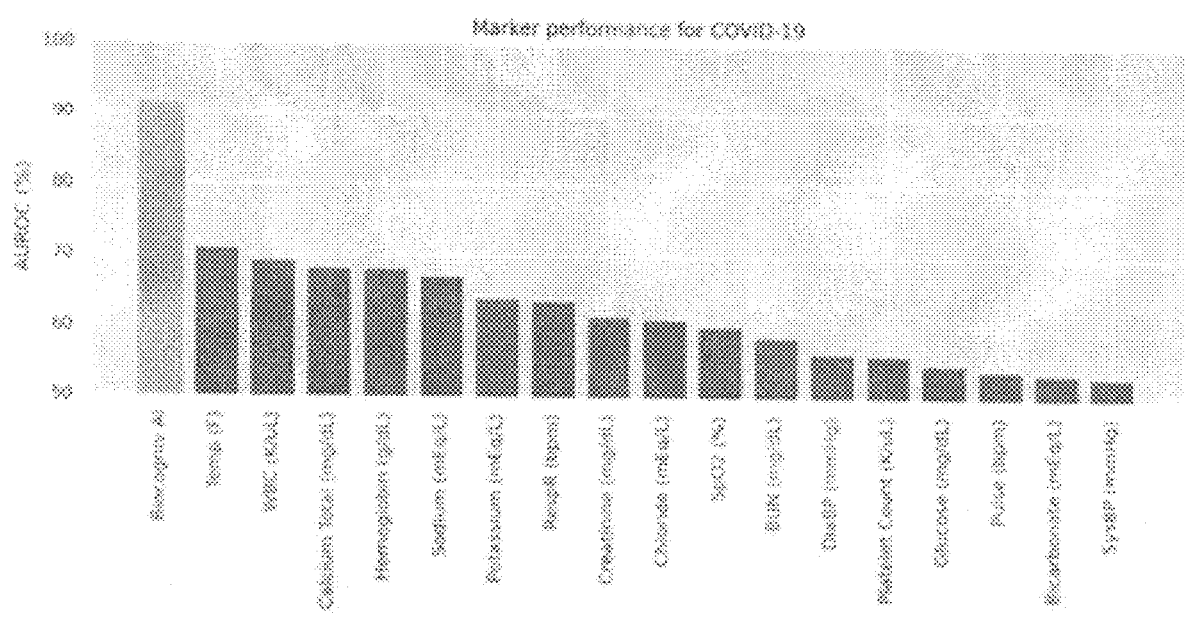
FIG. 9 is a graph showing how the area under the receiver operating characteristic curve (AUROC) performance varies with each input if it were a standalone blood test compared with the aggregation of all the listed inputs using the Biocogniv AI.

Some subject parametric data contributes more than others, as shown with the area under the receiver operating characteristic curve (AUROC) performance shown of FIG. 9, which shows AUROC results for each input parameter individually, as well as the much higher score from the COVID-19 model, which aggregates contribution from all the parametric data.

Figure 10:
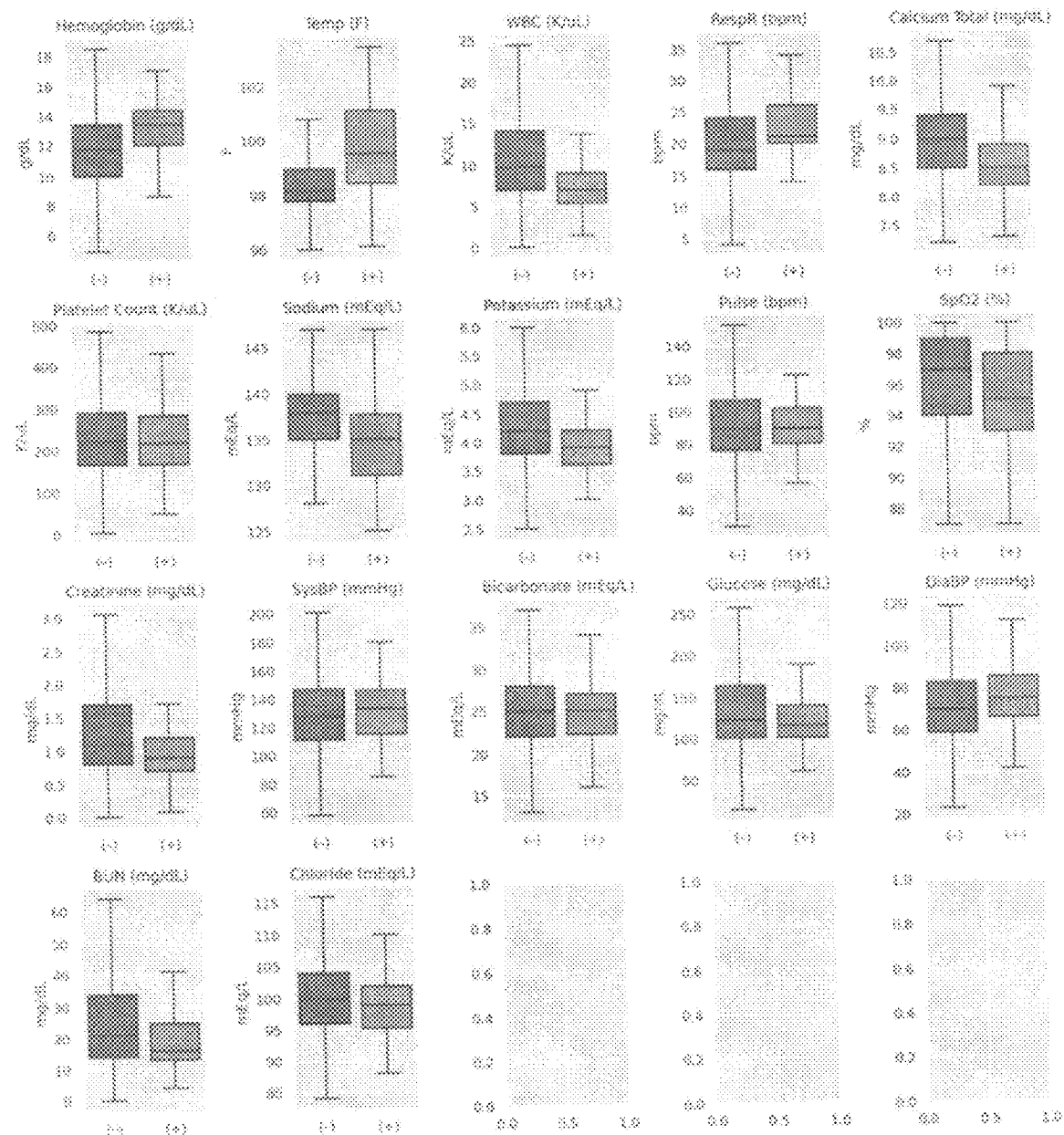
FIG. 10 is a set of boxplots of each input individually, by positive and negative COVID-19 status.

The boxplots of FIG. 10 show that the data for each parameter individually is very similar for subjects who are COVID-19 positive and negative according to their PCR tests. Thus, no one parameter was sufficiently discriminatory to identify COVID-19 in a patient.

While, as shown in FIGS. 9 and 10, no single input parameter by itself was able to distinguish COVID-19 positive from negative with great accuracy, the automated system of the present patent application, with its COVID-19 model generated by aggregating multiple parameters of data from the routinely collected blood tests, was very successful in classifying subjects as positive or negative for COVID-19, achieving an AUROC greater than 90%.

Figure 11:
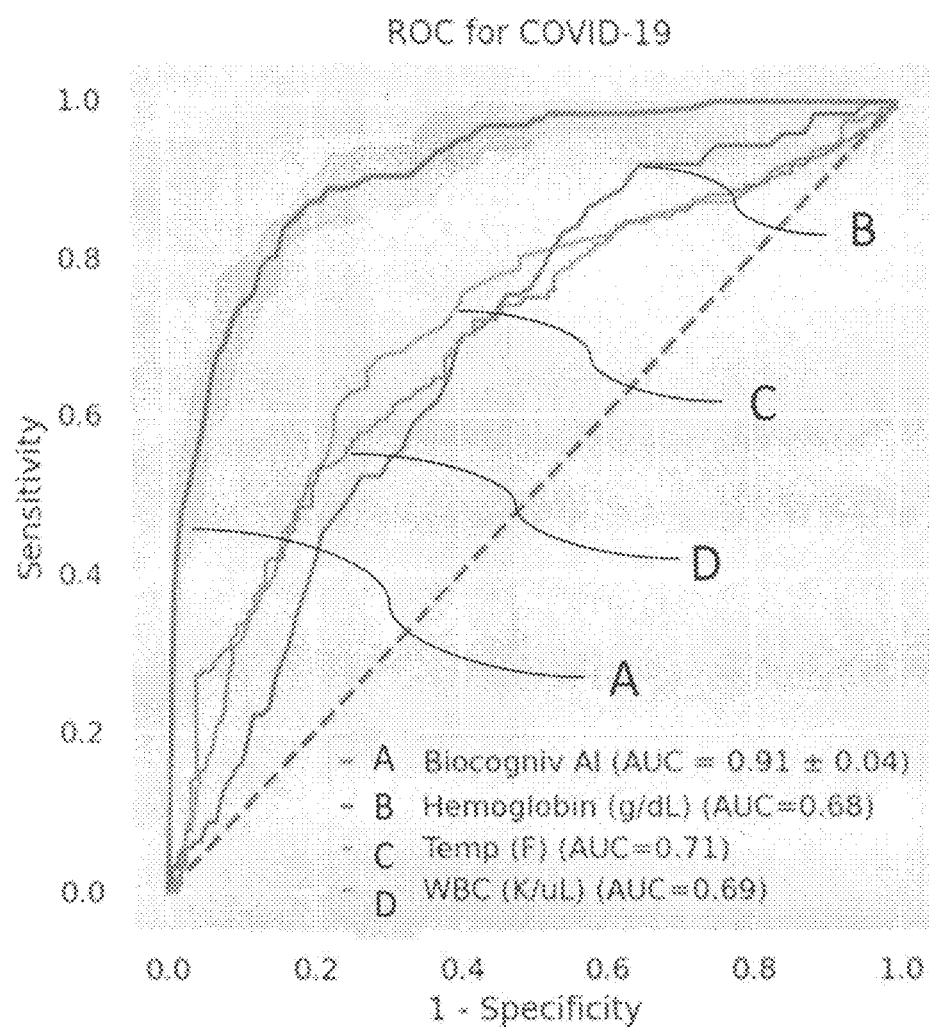
FIG. 11 is a chart comparing the receiver operating characteristic (ROC) curve for the COVID-19 model, with the ROC curves for the results of the three most predictive individual blood tests that were included as input data in the model.

The described method provided an AUROC of 91%, as shown in FIG. 11. A perfect diagnostic device would have a sharp curve in FIG. 11, with an edge extending near the top-left corner and an AUROC of 100%. The results shown are an average over five training-validation cycles with disjoint datasets ("5-fold cross-validation"). The quoted error for the AUROC for the model using all patient input data is two times the standard deviation and is depicted as the grey area around the left-most curve. For comparison, the top three inputs by importance, as ranked by the COVID-19 model, are also shown.

A table showing sensitivity and specificity for the COVID-19 model as a function of the score threshold used to generate the ROC curve of FIG. 6, is shown in FIG. 12. The table shows that the COVID-19 model is capable of achieving high sensitivity or high selectivity, depending on the threshold selected.

Figure 13:
FIG. 13 illustrates a typical k-fold cross validation with k=5 for training and independent validation.

The results shown in FIGS. 9-12 were obtained by splitting the full dataset of more than 6,000 emergency department encounters into five disjoint sets of independent training and validation data and running the training and validation steps five times, as per common practice in data science ("k-fold cross-validation"), as shown in FIG. 13. Rather than separating the dataset into training and validation blocks only once, for k-fold CV one does this k times, each time choosing a disjoint validation set from the training set. Provided no "parameter tuning" is performed in these steps—and in the present case, no tuning was performed at all—this method is statistically superior to using a single independent validation dataset and enables the empirical estimation of standard errors.

Figure 14:
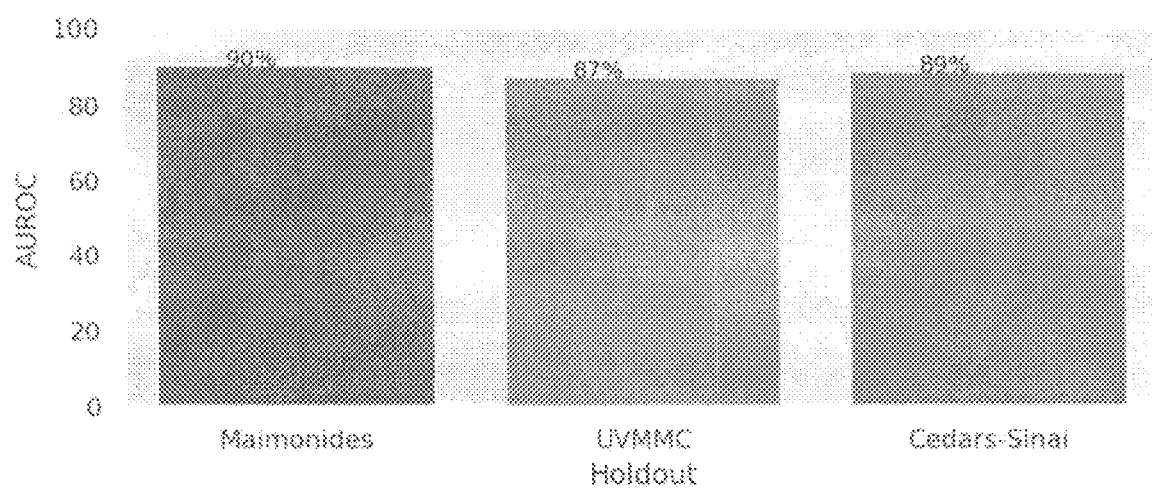
FIG. 14 illustrates performance of one embodiment of a COVID-19 model on three independent validation sets.

Traditional independent validation is shown in FIG. 14. The model was trained on the sites not reporting positive COVID-19 data and tested on sites reporting positive cases UVMMC, Cedars-Sinai, and Maimonides, to obtain the shown AUROCs of 90%, 87%, and 89% respectively. Thus, the model generalizability to sites other than the ones the model was trained on was illustrated.

Of particular relevance is the observation that the score is proportional to the likelihood of the patient being COVID-19 positive, as shown in FIG. 7. Having this linear relationship between score and likelihood of disease makes the score easier for the physician to interpret and to combine with vital signs, history, and symptoms in order to guide further testing and/or patient isolation. For example, a score of 80 may itself raise enough suspicion to justify patient isolation and prioritize further testing.

The present applicants found, in the populations studied, that two presumptive groups (scores >90 and scores <10) make up approximately half of the analyzed population. For the remainder of the population (Scores between 10-90), the score tracked the likelihood of the patient being positive. Due to its reliance on routinely collected patient data, abundantly available supplies, rapid test results, and independent mode of specimen collection, the COVID-19 model is particularly useful in health systems experiencing shortage of molecular/PCR test supplies, long test turnaround times, and/or high false negative rates in nasopharyngeal swabs.

Additional so-far non-routine tests may also be employed when they become available, are included among the existing routine tests, and are incorporated in the machine learning models.

Figure 15:
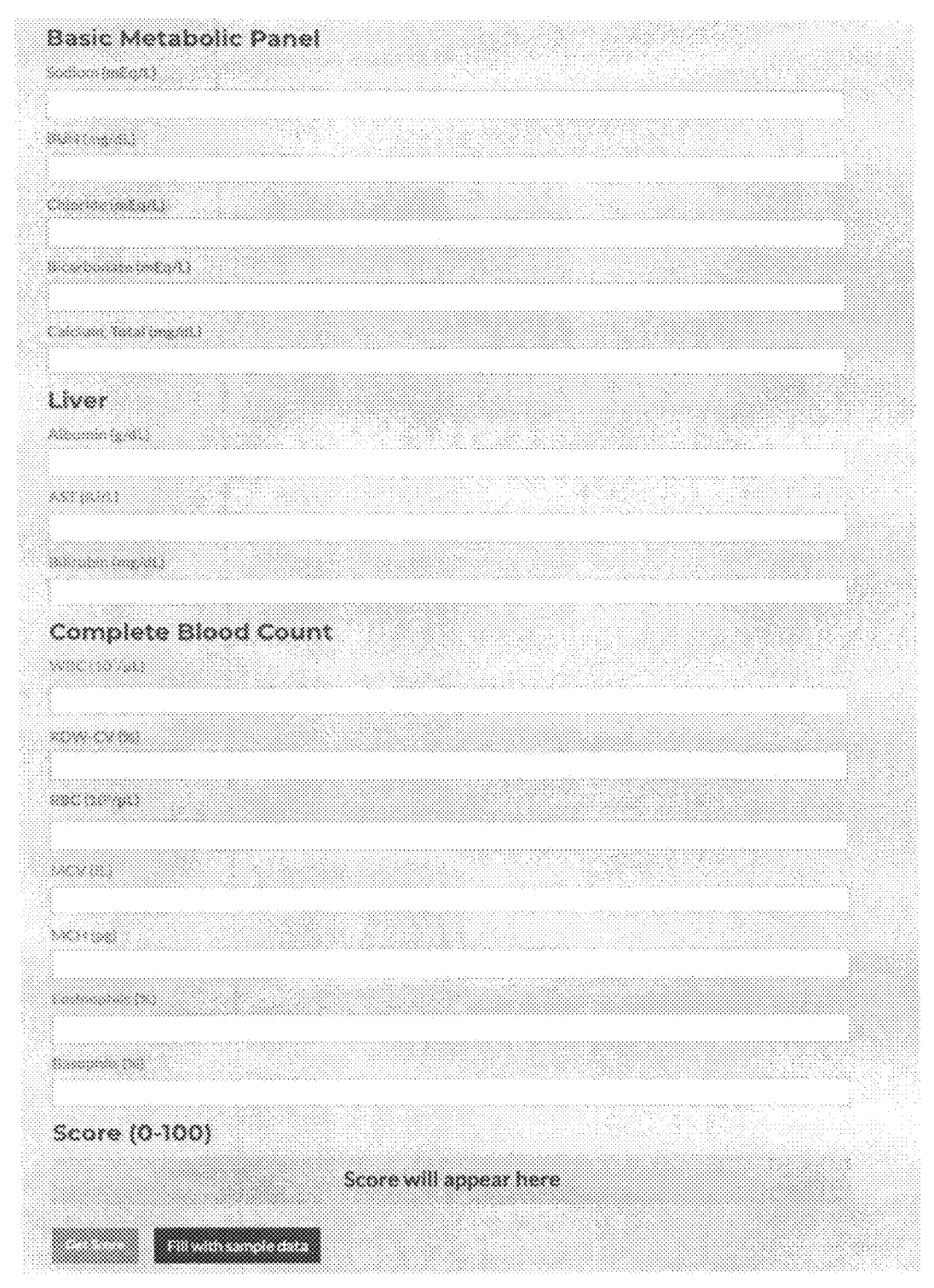

In addition to the method described herein below, that feeds a full set of patient vitals and BMP and CBC blood panel data into the machine learning model, the present inventors developed an app that can be used in situations where a patient's electronic medical record may not exist or is not available. One embodiment of the app can run on a smart phone or in a web browser, as shown in FIG. 15. The present inventors found that a previously identified reduced set of the routinely-collected data may be entered into the app on the phone by hand for COVID-19 scoring. The reduced data set omits those routinely-collected data that had low to negligible weight in the machine learning model, enabling faster manual data entry. For COVID-19 the present inventors found that the features with the largest calculated importance were eosinophils, calcium, and aspartate aminotransferase (AST).

One embodiment of the reduced set of vitals and tests from the blood panels includes the following tests:
Heart Rate (bpm)
Resp Rate (bpm)
Systolic BP (mmHg)
Diastolic BP (mmHg)
Temperature (° F. or ° C., oral, aural or scanning or rectal)
Sodium (mEq/L)
Potassium (mEq/L)
Bicarbonate (mEq/L)
Calcium, Total (mg/dL)
White Blood Cells (K/uL)
Hemoglobin (g/dL)
Platelet Count (K/uL)

Another embodiment of a reduced set of blood tests includes these 15 tests from the BMP, LFT, and CBC with differential:
Albumin
Asparate Aminotransferase (AST)
Basophils (%)
Bicarbonate
Bilirubin total
Calcium, Total
Chloride
Eosinophils (%)
MCH (Mean Corpuscular Hemoglobin)
MCV (Mean Corpuscular Volume)
RDW (Red Cell Distribution Width)
Red Blood Cell Count
Sodium
Urea Nitrogen
White Blood Cell Count Once entered through the app interface on a smartphone, the app then automatically feeds the reduced data set of data into the machine learning model, which may either be in the cloud or on the smartphone, and which provides the diagnostic score on the smartphone, as also shown in FIG. 15.

While several embodiments, together with modifications thereof, have been described in detail herein and illustrated in the accompanying drawings, it will be evident that various further modifications are possible without departing from the scope of the invention as defined in the appended claims. Nothing in the above specification is intended to limit the invention more narrowly than the appended claims. The examples given are intended only to be illustrative rather than exclusive.

What is claimed is:

1. A method of determining the risk of developing a known disease or condition or of identifying the presence of the known disease or condition in a subject, comprising:

training a machine learning model with basic metabolic panel (BMP) and complete blood count with different (CBC w/diff) data obtained from a positive group of training subjects who received a diagnosis of the known disease or condition, the known disease or condition comprising COVID-19 or sepsis, and from a negative group of training subjects who were not diagnosed to have the known disease or condition, wherein the machine learning model is trained to classify the subject data and determine a diagnostic score predicting a likelihood of a person having COVID-19 or sepsis, wherein machine learning comprises a support vector machine or a neural network, and wherein training the machine learning model comprises:
 iteratively training the machine learning model on different input sets of features;
 determining the model performance for each input data set of the different input sets of features; and
 excluding from the machine learning model features that do not improve performance of the machine learning model;

presenting a user interface for display, the user interface comprising a first section including fields associated with a BMP for a subject, a second section including fields associated with a liver function test (LFT) and a third section including fields associated with a CBC w/diff for the subject;

obtaining, via the user interface, subject data, wherein said subject data includes results of tests, wherein said tests include a BMP with a first set of multiple data parameters obtained from the fields of the first section, an LFT with a set second set of multiple data parameters obtained from the fields of the second section, and a CBC w/diff panel with a third set of multiple data parameters obtained from the fields of the third section, wherein the first set of multiple data parameters comprise at least a calcium value, wherein the second set of multiple data parameters include at least an aspartate aminotransferase value, and wherein the third set of multiple data parameters comprise at least a white blood cell count, an eosinophils value, and a red blood cell count;

inputting the first set of multiple data parameters, the second set of multiple data parameters and the third set of multiple data parameters into the trained machine learning model, and classifying, via the trained machine learning model, the subject data with respect to the risk of the subject having or developing the known disease or condition by using the subject data in the trained machine learning model;

determining, via the trained machine learning model a diagnostic score, the diagnostic score predicting the likelihood of the subject having COVID-19 or the diagnostic score predicting the likelihood of the subject having sepsis; and providing for display the diagnostic score via the user interface.

2. The method as recited in claim 1, wherein said subject data consists of said BMP and said CBC w/diff results.

3. The method as recited in claim 2, wherein said subject data consists of selected ones of said BMP and said CBC results.

4. The method as recited in claim 1, wherein said classifying uses BMP and CBC results obtained from a single drawing of subject blood.

5. The method as recited in claim 1, wherein said subject data further includes results of at least one from the group consisting of the liver function blood test panel, subject vitals, and subject demographic data.

6. The method as recited in claim 1, wherein said subject data further includes results of at least one from the group consisting of urine analysis, medical history, medical review of systems, a chest pain panel, an abdominal pain panel, and a traumatic brain injury panel.

7. The method as recited in claim 1, wherein the known disease or condition includes at least one from the group consisting of COVID-19, sepsis, pulmonary embolism, diabetic keto-acidosis, pyelonephritis, congestive heart failure, dehydration, syndrome of inappropriate ADH, renal insufficiency, pneumonia, myocardial infarction and hematological conditions, and blood dyscrasias.

8. The method as recited in claim 1, further comprising drawing a sample of subject blood, performing said blood test panels on said sample, automatically storing said subject data in the subject's electronic medical record, and using said stored subject data in said classifying step.

9. The method as recited in claim 1, further comprising drawing a sample of subject blood, performing said blood test panels on said sample, manually entering at least a subset of said subject data in an app on a smartphone, wherein said entered subset of said subject data is used in said classifying step.

10. The method as recited in claim 1, wherein said classification includes a disease or condition score, wherein said disease or condition score is related to at least one from the group consisting of probability of the subject having or developing the disease or condition, probability of the subject developing a complication of the disease or condition, and probability of the subject developing a defined outcome.

11. The method as recited in claim 10, wherein said defined outcome includes at least one from the group consisting of respiratory insufficiency and death.

12. The method as recited in claim 10, further comprising providing a report of subject data, wherein said disease or condition score is included in said report.

13. The method as recited in claim 12, further comprising providing a threshold score in said report, and further comprising highlighting said disease or condition score in said report if said disease or condition score is higher than said threshold score.

14. The method as recited in claim 13, further comprising defining said threshold score so that at least twice as many subjects with a score higher than the threshold score are likely to have or be at risk of having the disease or condition as subjects who are free of the disease.

15. The method as recited in claim 13, wherein if said disease or condition score is above said threshold score automatically performing at least one test on the sample of subject blood.

16. The method as recited in claim 15, wherein said further test includes at least one from a group consisting of a lactate test and a procalcitonin test.

17. The method as recited in claim 13, wherein if said disease or condition score is above said threshold score providing a treatment to the subject.

18. The method as recited in claim 17, wherein said treatment includes at least one from the group consisting of providing antibiotics, antiviral medication, antifungal medication, oxygen tube, a face mask, or mechanical ventilation, transfusion, a steroid, vasopressor medication, surgery, antibiotics, antiviral medication, an anticoagulant, a steroid, an immunosuppressant, vasopressor medication, convalescent plasma, intravenous fluids, high flow nasal cannula, mechanical ventilation, non-invasive ventilation, transfusion or self-proning oxygenation.

19. The method as recited in claim 17, further comprising obtaining a second subject data, wherein said second subject data includes results of BMP and CBC panels from blood drawn after said treatment, and further comprising repeating said classifying step (b) on said second subject data and determining a second disease or condition score to evaluate said treatment.

20. The method as recited in claim 1, further comprising obtaining a second subject data, wherein said second subject data includes results of BMP and CBC panels from blood drawn at a second time, further comprising documenting said second time, and further comprising determining a rate at which at least one parameter of said subject data changed, and using said rate within said machine learning classification system.

21. The method as recited in claim 20, further comprising obtaining a third subject data, wherein said third subject data includes results of BMP and CBC panels from blood drawn at a third time, further comprising documenting said third time, and further comprising determining a rate that the rate said at least one parameter of said subject data changes, and using said rate that the rate changes within said machine learning classification system.

22. The method as recited in claim 1, further comprising providing training of said machine learning classification system, wherein said training includes providing BMP and CBC data to a machine learning program from electronic medical records of subjects who received a diagnosis of the disease or condition and from electronic medical records of subjects who were not diagnosed to have the disease or condition.

23. The method as recited in claim 22, further comprising establishing eligibility criteria for data from electronic medical records to be included in said training of said machine learning classification system.

24. The method as recited in claim 1, wherein said positive group and said negative group each include at least 200 samples.

25. The method as recited in claim 1, wherein said positive group and said negative group include data from at least a dozen hospitals, and a plurality of racial groups.

26. The method as recited in claim 1, wherein said subject data further includes at least two from the group consisting of demographic data, urinalysis data, medical history data, medical review of systems data, family history data, enzyme levels data, hormone levels data, biomarkers data, chest pain blood test panel data, abdominal pain blood test panel data, and traumatic brain injury blood test panel data.

27. The method as recited in claim 1, wherein said subject data further includes at least three from the group consisting of demographic data, urinalysis data, medical history data, medical review of systems data, family history data, enzyme levels data, hormone levels data, biomarkers data, chest pain blood test panel data, abdominal pain blood test panel data, and traumatic brain injury blood test panel data.

28. The method as recited in claim 1, wherein said subject data further includes at least four from the group consisting of demographic data, urinalysis data, medical history data, medical review of systems data, family history data, enzyme levels data, hormone levels data, biomarkers data, chest pain blood test panel data, abdominal pain blood test panel data, and traumatic brain injury blood test panel data.

29. The method as recited in claim 1, wherein said subject data further includes one or more descriptor-number entries modified by a number indicating at least one from a group consisting of duration and intensity of at least one from a group consisting of a prior disease, condition, exposure, and medication.

* * * * *